United States Patent [19]

Aberle et al.

[11] 4,204,117
[45] May 20, 1980

[54] SAMPLE ANALYZER

[75] Inventors: Lothar Aberle, Sindorf; Walter Bank, Cologne; Franz Hillenkamp, Frankfurt; Raimund Kaufmann, Düsseldorf-Meerbusch; Rainer Nitsche, Frankfurt; Eberhard Unsöld, Munich; Reiner Wechsung, Cologne, all of Fed. Rep. of Germany

[73] Assignee: Leybold-Heraeus GmbH, Köln-Bayental, Fed. Rep. of Germany

[21] Appl. No.: 938,329

[22] Filed: Aug. 30, 1978

[30] Foreign Application Priority Data

Sep. 3, 1977 [DE] Fed. Rep. of Germany ....... 2739828

[51] Int. Cl.² .............................................. B01D 59/44
[52] U.S. Cl. ................................ 250/287; 250/361 C; 250/423 P; 250/461 B
[58] Field of Search ..................... 250/281, 287, 423 P, 250/311, 361 C, 461 B; 350/81; 356/317, 318

[56] References Cited

U.S. PATENT DOCUMENTS

| | | | |
|---|---|---|---|
| 3,782,823 | 1/1974 | Kantorski | 350/81 |
| 3,972,616 | 8/1976 | Minami | 350/81 |
| 4,018,530 | 4/1977 | Hirschfeld | 356/317 |

*Primary Examiner*—Harold A. Dixon
*Attorney, Agent, or Firm*—Spencer & Kaye

[57] ABSTRACT

A sample analyzer includes a microscope for alternatively focusing an electromagnetic radiation on the sample to cause ion emission therefrom and visually observing the sample; a mass spectrometer for the mass analysis of the emitted ions; an illuminating device for lighting the sample for the microscopic visual observation thereof; an ion optical system for directing the emitted ions into the mass spectrometer; and a displaceably supported carrier carrying the ion optical system and at least one part of the illuminating device. The carrier has a first position in which the ion optical system is in an operating position in alignment with the sample and a second position in which the illuminating device is in an operating position in alignment with the sample. There is further provided an actuator for selectively moving the carrier into its positions in a direction generally perpendicular to the axis of the ion optical system.

12 Claims, 1 Drawing Figure

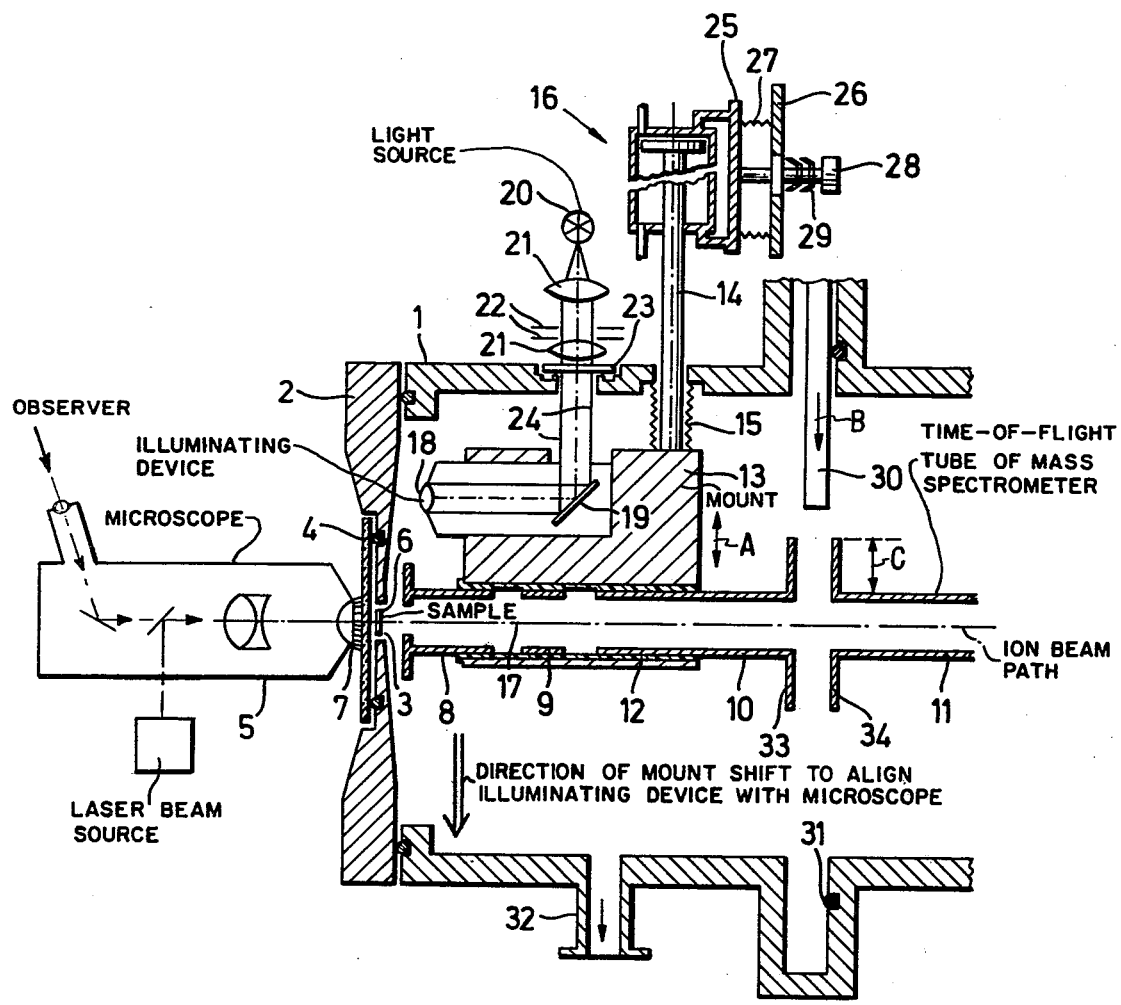

SAMPLE ANALYZER

BACKGROUND OF THE INVENTION

The present invention relates to an apparatus for irradiating a sample by an electromagnetic beam, preferably a pulsed laser beam, and for performing a subsequent mass analysis of the ions generated by the irradiation. The apparatus includes a microscope for focusing the laser beam as well as for observing the sample, and further has a mass spectrometer and illuminating means operatively coupled to the sample in a selective manner.

An apparatus of the above-outlined type serves primarily to examine thin sections for physiological and biomedical uses, but is suitable as well for analyzing any other type of thin samples. It is a particular advantage of such an apparatus that extremely small sample zones (for example, in the order of magnitude of cell components of biological substances) can be irradiated and analyzed. In order to be able to direct the laser beam to such small sample zones and to correlate the locus of analysis with the morphologic structure of the sample, the latter has to be observed with a microscope, particularly in transillumination. Moreover, devices for setting interference, phase and polarization contrasts and the like are desirable. Thus far, however, meeting the requirement of an examination by microscope has, in practice, encountered considerable difficulties, since the means for transillumination as well as the entrance opening of the means for mass analysis of the ions must be located very close to the sample. For this reason transillumination of the sample has often been renounced and only reflected illumination means were provided. In reflected light, however, cells disposed in a sample section are very difficult to distinguish.

German Pat. No. 2,141,387 discloses an arrangement which includes a monitor, an illumination device, a mass spectrometer and a device for observing luminescence. These devices are mounted together on a turret and thus can be selectively swung into an operating position. Such a device, however, involves prohibitive manufacturing costs, particularly if—as it is often the case—a time-of-flight tube of more than 2 m long is used as the mass separating system and if all these devices must be disposed in a vacuum chamber. Time-of-flight spectroscopy, in particular, has been found to the especially suitable for the examination of organic samples by laser beam irradiation not only because of the high resolution and a high probability of detection, but primarily because the total element information is available immediately after each laser bombardment.

The periodical "Analusis", in issue No. 3 of 1976, on pages 115–119 discloses a pivotal prism which can be swung into its operating position for directing the light required for transillumination onto the sample from a light source disposed outside the mass spectrometer. In this device, the essential lens systems are also disposed outside the mass spectrometer, that is, relatively far from the sample, so that a greatly enlarged observation of the sample in transillumination is not feasible.

SUMMARY OF THE INVENTION

It is an object of the present invention to provide an improved apparatus of the above-described type in which an examination of the sample under transillumination and great magnification, as well as the use of a time-of-flight mass spectrometer can be effected in a technically simple manner.

This object and others to become apparent as the specification progresses, are accomplished by the invention, according to which, briefly stated, the sample analyzer includes a microscope for alternatingly focusing an electromagnetic radiation on the sample to cause an ion emission therefrom and visually observing the sample; a mass spectrometer for the mass analysis of the emitted ions; an illuminating device for lighting the sample for the microscopic visual observation thereof; an ion optical system for directing the emitted ions into the mass spectrometer; and a displaceably supported carrier carrying the ion optical system and at least one part of the illuminating device. The carrier has a first position in which the ion optical system is in an operating position in alignment with the sample and a second position in which the illuminating device is in an operating position in alignment with the sample. There is further provided an actuator for selectively moving the carrier into its positions in a direction generally perpendicular to the axis of the ion optical system.

In an apparatus of the above-defined structure, the parts which must be moved during the change-of-place of the ion optical system and the illuminating device have a relatively small mass so that they can be moved back and forth between their end positions with the highest mechanical precision, yet without complex arrangements. Since only the ion optical system (and not the entire mass spectrometer) need be moved, it is feasible to use a time-of-flight mass spectrometer, since the long time-of-flight tube itself need not be displaced. In the other position, a lens system can be brought into the immediate vicinity of the sample (that is, at a distance of only a few millimeters); this permits a greatly enlarged observation of the sample in transillumination.

According to an advantageous embodiment of the invention, an essentially cylindrical vacuum chamber is provided for the mass spectrometer and one of the frontal faces of the chamber housing has an opening which is closed vacuum-tight by means of a covering glass. The microscope is disposed on the outside of the covering glass, while the sample is situated on the inside thereof. The ion optical system as well as the illuminating means are mounted to be shiftable or swingable as a unit with the aid of an actuating rod which laterally protrudes from the housing in a vacuum-tight manner. Displacement is expediently effected by an electropneumatic drive which ensures high-precision movement and which further permits sufficient damping.

According to a further advantageous feature of the invention, only a lens or a lens system as well as a mirror of the sample-illuminating means are displaceably disposed in the interior of the housing and the other components, such as the light source, condenser, aperture, field aperture, achromatic lens, operating elements and the like are disposed outside of a window arranged in the wall of the housing. This arrangement ensures that the mass of the components to be displaced are considerably reduced. It is feasible to introduce the light into the vacuum chamber by means of a light conductor.

Since it is necessary in all cases to physically separate the ion optical system from the mass spectrometer, the distance between the end of the ion optical system and the time-of-flight tube can be so selected that a closing plate can be moved through the clearance. This sliding plate can separate in a vacuum-tight manner the frontal space containing the sample, from the relatively large space in which, for example, the time-of-flight tube and the ion detector are disposed.

During the exchange of samples it is then necessary to de-vacuumize only a very small space which can again rapidly be brought back to the desired vacuum pressure. Contamination of the detector (mass spectrometer) during the admission of air can thus also be substantially avoided.

BRIEF DESCRIPTION OF THE DRAWING

The sole FIGURE is a schematic sectional view of a preferred embodiment of the invention.

DESCRIPTION OF THE PREFERRED EMBODIMENT

Turning now to the FIGURE, there is shown a part of an essentially cylindrical housing 1, whose illustrated front end is closed in a vacuum-tight manner by a lid 2 which has an opening 3 closed (also in a vacuum-tight manner) by means of a covering glass 4. On the outside of the covering glass 4 there is arranged a microscope 5 with which the sample disposed at the inner side of the covering glass 4 can be observed and a laser beam, which causes the emission of ions by the sample 6, can be focused onto the sample. In order to improve the optical contact, a layer 7 consisting of an immersion liquid is provided between the condenser lens of the microscope 5 and the covering glass 4. Such an arrangement is of particular advantage when objectives with high resolving power are used.

An ion optical system comprising cylindrical tube sections 8, 9, 10 and a time-of-flight tube 11, of which only the front end is shown and which forms part of a mass spectrometer, are disposed in the interior of the housing 1. The tube sections (lenses) 8, 9, 10 are fastened to a displaceable carrier mount 13 by means of a plastic sleeve 12. The voltage supply for the ion optical system is not shown. The tube section 10 may be part of the time-of-flight tube.

To the mount 13 there is attached a drive rod 14 which projects laterally from the housing 1 through an opening which is sealed in a vacuum-tight manner with respect to the inside of the vacuum chamber by means of bellows 15 coaxially surrounding the drive rod 14 and attached to the mount 13 and the chamber housing 1. The drive rod 14 is the piston rod of power cylinder unit 16 which is illustrated schematically and with which the mount 13 can be moved back and forth between two end positions in the direction of the double-headed arrow A, generally perpendicularly to the axis 17 of the ion optical system. In the position shown in the drawing, the ion optical system is disposed directly behind the sample 6. In this end position, the axis 17 of the ion optical system coincides with the optical axis of the microscope and with the axis of the time-of-flight tube 11. While the illustrated driving arrangement effects a linear displacement of the mount 13, it is to be understood that a drive causing pivotal motion of the mount 13 between the end positions can be provided.

The mount 13 further supports a lens 18 or a lens system and a mirror 19. These components are part of a device for illuminating the sample. Additional components of the illuminating device, such as the light source 20, the lenses 21 (collector lens, achromatic lens) and the apertures 22 (aperture and field aperture) are disposed outside of housing 1. A window 23 is provided for the passage of the light emanating from source 20 into housing 1.

For observing the sample 6 in transillumination with the aid of microscope 5, the mount 13 is shifted downwardly (as viewed in the FIGURE) in the direction A into the second end position (not shown) in which the lens 18 is disposed in the immediate vicinity of the sample 6. The beam path indicated in the drawing by lines 24 shows that in this position the light emanating from source 20 is reflected by the mirror 19 and impinges on the sample 6 so as to permit observation through the microscope 5 under transillumination. The axis of the lens 18 and thus of the beam path 24 then coincides with the axis of the microscope 5.

The power cylinder unit 16 and preferably also the components 20, 21, 22 of the sample illuminating device which components are disposed outside of housing 1, are mounted together on a plate 25 which itself is supported on a spring bed. For forming the spring bed, a fixed plate 26 is provided which is connected to the plate 25 by means of springs 27 and a bolt 28. The bolt 28 is supported on the plate 26 by means of disc springs 29, so that the plate 25 and thus the position of components 13-16 and 18-22 fastened therto can be set precisely with the aid of adjusting screws (not shown). The preferably adjustable abutments for the two end positions of the mount 13 are also not shown for the sake of clarity.

The tube section 10 is spaced from the time-of-flight tube 11 at such a distance that a closing plate 30 of a slide, which is shown only in part, can be pushed through the clearance formed therebetween. If access has to be gained to the shown front end of the vacuum chamber 1, for example, for exchanging the sample, and thus de-vacuumization has to occur, the plate 30 is lowered in the direction of the arrow B into its closed position in which it lies against a seal 31 and thus vacuum-tightly separates the front section of housing 1 in which the sample 6 and the displaceable mount 13 are disposed, from the remaining interior of the housing 1 where the relatively long time-of-flight tube 11 and the ion detector (not shown) are disposed. Thus it is possible, when exchanging samples 6, to admit air to only a very small portion of the interior of housing 1 which then, after the samples have been exchanged, can be evacuated again very quickly to the desired pressure with the aid of a vacuum pump connected to the nipple 32.

The facing ends of the pipe section 10 and the time-of-flight tube 11 have respective collars 33 and 34 which prevent undesirable field interference from occuring in the tube sections 10 and 11. The width C of the collars 33 and 34 depends on the distance between them and on the diameter of the tube sections 10, 11. The width C approximately corresponds to the diameter of the tube sections 10 and 11.

It is to be understood that the above description of the present invention is susceptible to various modifications, changes and adaptations, and the same are intended to be comprehended within the meaning and range of equivalents of the appended claims.

What is claimed is:

1. In a sample analyzer including a microscope for focusing an electromagnetic radiation on the sample to cause ion emission therefrom and visually observing the sample; a mass spectrometer for the mass analysis of the emitted ions; an illuminating means for lighting the sample for the microscopic visual observation thereof; the improvement comprising (a) an ion optical system for directing ions emitted by the sample into the mass spectrometer;

(b) displaceably supported carrier means carrying said ion optical system and at least one part of said illuminating means; said carrier means having a first position in which said ion optical system is in an operating position in alignment with the sample and a second position in which said illuminating means is in an operating position in alignment with the sample; and (c) actuating means for selectively moving said carrier means into said positions in a direction generally perpendicular to the axis of said ion optical system.

2. A sample analyzer as defined in claim 1, wherein said mass spectrometer is a time-of-flight mass spectrometer.

3. A sample analyzer as defined in claim 1, wherein said illuminating means comprises a light conductor.

4. A sample analyzer as defined in claim 1, further comprising a housing defining a vacuum chamber accommodating said carrier means, said ion optical system, said part of said illuminating means and said mass spectrometer; an opening in one end of the housing; a covering glass sealingly closing off said opening and having an inner face being disposed in the vacuum chamber and an outer face being disposed externally thereof; the sample and the microscope being situated at said inner face and at said outer face, respectively; said actuating means comprising a rod attached to said carrier means and sealingly projecting from said housing.

5. A sample analyzer as defined in claim 4, further comprising means for linearly displaceably supporting said carrier means.

6. A sample analyzer as defined in claim 4, further comprising a closing plate slidably supported by said housing and movable into said vacuum chamber into a closed position in which it sealingly divides said vacuum chamber into a first chamber part accommodating said ion optical system and a second chamber part accommodating said mass spectrometer; said ion optical system and said mass spectrometer having facing ends arranged at a clearance providing an unobstructed traveling path for said closing plate.

7. A sample analyzer as defined in claim 4, wherein said mass spectrometer is a time-of-flight mass spectrometer including a time-of-flight tube disposed in said vacuum chamber; said ion optical system comprises a plurality of axially aligned tubes constituting lenses; said ion optical system and said time-of-flight tube having facing ends each carrying a collar having a width approximately corresponding to the diameter of said tubes.

8. A sample analyzer as defined in claim 4, wherein said actuating means further comprises a pneumatic power cylinder unit and wherein said rod constitutes a piston rod of said unit.

9. A sample analyzer as defined in claim 8, further comprising a spring bed supporting said unit.

10. A sample analyzer as defined in claim 4, wherein said illuminating means comprises first components including a light source and a first lens system; said first components being disposed externally of said housing; and second components including a reflecting mirror and a second lens system; said second components constituting said part of said illuminating means mounted on said carrier means; and a window in said housing for effecting passage, into said vacuum chamber, of a light beam emanating from said light source and directed onto said reflecting mirror; said second lens system being in alignment with the sample and the microscope in said second position of said carrier means.

11. A sample analyzer as defined in claim 10, wherein said second lens system consists of a single lens.

12. A sample analyzer as defined in claim 10, further comprising a spring bed supporting said first components of said illuminating means.

* * * * *